(12) United States Patent
Guevremont et al.

(10) Patent No.: US 6,713,758 B2
(45) Date of Patent: Mar. 30, 2004

(54) SPHERICAL SIDE-TO-SIDE FAIMS

(75) Inventors: Roger Guevremont, Ottawa (CA); Randy Purves, Orleans (CA); David Barnett, Orleans (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 10/359,644

(22) Filed: Feb. 7, 2003

(65) Prior Publication Data

US 2003/0226965 A1 Dec. 11, 2003

Related U.S. Application Data (63) Continuation-in-part of application No. 09/762,239, filed on Jun. 28, 2001, which is a continuation of application No. 09/321,820, filed as application No. PCT/CA99/00715 on Aug. 5, 1999, now Pat. No. 6,504,149

(60) Provisional application No. 60/095,481, filed on Aug. 5, 1998, and provisional application No. 60/354,711, filed on Feb. 8, 2002.

(51) Int. Cl.[7] .......................... H01J 49/00; H01J 49/40; B01D 59/44

(52) U.S. Cl. ...................... 250/290; 250/281; 250/288; 250/287; 250/291

(58) Field of Search .............................. 250/290, 291, 250/281, 288, 287

(56) References Cited

U.S. PATENT DOCUMENTS 6,504,149 B2 * 1/2003 Guevremont et al. ....... 250/286
2003/0057367 A1 * 3/2003 Guevremont et al. ....... 250/281

* cited by examiner

*Primary Examiner*—Nikita Wells
(74) *Attorney, Agent, or Firm*—Freedman & Associates (57) ABSTRACT

A high field asymmetric waveform ion mobility spectrometer (FAIMS) having spherical electrode geometry is disclosed. The spherical FAIMS includes an inner generally spherical electrode supported in a spaced-apart arrangement relative to an outer electrode. The outer electrode has a curved inner surface that maintains an approximately uniform spacing to the inner electrode. The space between the inner and outer electrodes defines an analyzer region, where an electric field is established by the application of an asymmetric waveform voltage and a direct current compensation voltage to at least one of the inner and outer electrodes. An ion inlet and an ion outlet are disposed within the curved inner surface of the outer electrode such that the shortest distance between the inlet and the outlet in any direction around the inner electrode is approximately a same distance.

17 Claims, 6 Drawing Sheets

SPHERICAL SIDE-TO-SIDE FAIMS

This application is a continuation-in-part of U.S. patent application Ser. No. 09/762,239 filed Jun. 28, 2001 which is a continuation of U.S. patent application Ser. No. 09/321,820 filed May 28, 1999 now U.S. Pat. No. 6,504,149 which is a National Stage of International Application No. PCT/CA99/00715 filed Aug. 5, 1999, which claims the benefit of U.S. Provisional Application No. 60/095,481 filed Aug. 5, 1998. This application also claims the benefit of U.S. Provisional Application No. 60/354,711 filed Feb. 8, 2002.

FIELD OF THE INVENTION

The instant invention relates generally to high field asymmetric waveform ion mobility spectrometry (FAIMS), more particularly the instant invention relates to FAIMS having spherical electrode geometry.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, N.Y., 1988) teach that at high electric field strength, for instance fields stronger than approximately 5,000 V/cm, the ion drift velocity is no longer directly proportional to the applied electric field, and K is better represented by $K_h$, a non-constant high field mobility term. The dependence of $K_h$ on the applied electric field has been the basis for the development of high field asymmetric waveform ion mobility spectrometry (FAIMS). Ions are separated in FAIMS on the basis of a difference in the mobility of an ion at high field strength, $K_h$, relative to the mobility of the ion at low field strength, K. In other words, the ions are separated due to the compound dependent behavior of $K_h$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_h$, lasting for a short period of time $t_h$ and a lower voltage component, $V_l$, of opposite polarity, lasting a longer period of time $t_l$. The waveform is synthesized such that the integrated voltage-time product, and thus the field-time product, applied to the second electrode during each complete cycle of the waveform is zero, for instance $V_h t_h + V_l t_l = 0$; for example +2000 V for 10 $\mu$s followed by −1000 V for 20 $\mu$s. The peak voltage during the shorter, high voltage portion of the waveform is called the "dispersion voltage" or DV.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_h = K_h E_h$, where $E_h$ is the applied field, and $K_h$ is the high field ion mobility under operating electric field, pressure and temperature conditions. The distance traveled by the ion during the high voltage portion of the waveform is given by $d_h = v_h t_h = K_h E_h t_h$, where $t_h$ is the time period of the applied high voltage. During the longer duration, opposite polarity, low voltage portion of the asymmetric waveform, the y-axis velocity component of the ion is $v_l = KE_l$, where K is the low field ion mobility under ambient pressure and temperature conditions. The distance traveled is $d_l = v_l t_l = KE_l t_l$. Since the asymmetric waveform ensures that $(V_h t_h) + (V_l t_l) = 0$, the field-time products $E_h t_h$ and $E_l t_l$ are equal in magnitude. Thus, if $K_h$ and K are identical, $d_h$ and $d_l$ are equal, and the ion is returned to its original position along the y-axis during the negative cycle of the waveform. If at $E_h$ the mobility $K_h > K$, the ion experiences a net displacement from its original position relative to the y-axis. For example, if a positive ion travels farther during the positive portion of the waveform, for instance $d_h > d_l$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the first or the second electrode. If ions derived from two compounds respond differently to the applied high strength electric fields, the ratio of $K_h$ to K may be different for each compound. Consequently, the magnitude of the CV that is necessary to prevent the drift of the ion toward either electrode is also different for each compound. Thus, when a mixture including several species of ions, each with a unique $K_h$/K ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

Guevremont et al. have described the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region in the annular gap between the cylindrical electrodes as a result of the electric fields which change with radial distance. Focusing the ions of interest has the effect of reducing the number of ions of interest that are lost as a result of the ion suffering a collision with one of the inner and outer electrodes. FAIMS devices with cylindrical electrode geometry have been described in the prior art, as for example in U.S. Pat. No. 5,420,424, the contents of which are incorporated herein by reference.

In WO 00/08455, the contents of which are incorporated herein by reference, Guevremont and Purves describe a domed-FAIMS analyzer. In particular, the domed-FAIMS analyzer includes a cylindrical inner electrode having a curved surface terminus proximate an ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, and in addition the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ions to travel towards the ion-outlet orifice, which advantageously also prevents the ions from migrating in a reverse direction, back towards the ion source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as described in greater detail by Guevremont and Purves in WO 00/08457, the contents of which are incorporated herein by reference.

Guevremont and Purves further disclose a near-trapping mode of operation for the above-mentioned domed-FAIMS analyzer, which achieves ion transmission from the domed-FAIMS to a mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions that are extracted from this region do so as a narrow, approximately collimated beam, which is pulled by the gas flow through the ion-outlet orifice and into a smaller orifice leading into the vacuum system of the mass spectrometer. Accordingly, a tandem domed-FAIMS/MS device is a highly sensitive instrument that is capable of detecting and identifying ions of interest at part-per-billion levels.

More recently, in WO 01/69216 the contents of which is incorporated herein by reference, Guevremont and Purves describe a so-called "perpendicular-gas-flow-FAIMS", which is identically referred to as a side-to-side FAIMS. The analyzer region of the side-to-side FAIMS is defined by an annular space between inner and outer cylindrical electrodes. In particular, ions that are introduced into the analyzer region of the side-to-side FAIMS are selectively transmitted in a direction that is generally around the circumference of the inner electrode. For instance, the ion inlet and the ion outlet of a side-to-side FAIMS device are disposed, one opposing the other, within a surface of the outer electrode such that an ion is selectively transmitted through the curved analyzer region between the ion inlet and the ion outlet along a continuously curving ion flow path absent a portion having a substantially linear component. In particular, the ion travels from the ion inlet to the ion outlet by flowing around the inner electrode in one of a "clock-wise" and a "counter clock-wise" direction. This is in contrast to the above-mentioned FAIMS devices in which the ions are selectively transmitted along the length of the inner electrode.

Advantageously, the side-to-side FAIMS device reduces the minimum distance that must be traveled by an ion within the analyzer region to approximately fifty per cent of the circumference of the inner electrode. Since the ions are divided into two streams traveling in opposite directions around the inner electrode after they are introduced through the ion inlet, the effective ion density within the analyzer region is reduced, and so too is the ion-ion repulsion space charge effect reduced. Furthermore, the reduction of the minimum ion travel distance has the added benefit of improving the ion transmission efficiency. For example, by keeping the time for travel short, the effect of diffusion and ion-ion repulsion forces are minimized. In keeping distances short, the transit time of the ions through the analyzer region is also short, which supports more rapid analysis of ion mixtures.

Of course, the side-to-side FAIMS device also has some limitations. For example, ion separation occurs only within a very small portion of the analyzer region of a side-to-side FAIMS. With only two possible ion flow directions through the analyzer region, the ion concentration at a point along either ion flow direction remains relatively high. As the ions transit the analyzer region, diffusion and ion-ion repulsion forces, even though they are small, cause the ions to spread out in a direction along the length of the inner and outer electrodes. Accordingly, the ions are introduced through the ion inlet as an approximately collimated beam of ions, but rapidly spread out to form a sheet of ions that travels around the inner electrode to the ion outlet. Furthermore, ions are focused between the inner and outer electrodes as a result of the application of the applied CV and DV, but this focusing occurs only in a direction that is approximately normal to the electrode surfaces, i.e. in a radial direction. As such, there is no force capable of focusing the ions in a direction that is parallel to the electrode surfaces, i.e. in a longitudinal direction. Since the ions spread out slightly during separation, some of the ions become entrained in portions of the analyzer region where the gas flow rate is low or stagnant. Consequently the ion transmission efficiency from the FAIMS to, for example, an external mass spectrometer is reduced.

Additionally, the strength of the focusing field between the inner and outer electrodes is related to the radius of the cylindrically shaped inner electrode. In order to produce stronger focusing fields, it is necessary to utilize an inner electrode with a smaller radius. Of course, a FAIMS analyzer having a smaller inner electrode also has a smaller available volume for separating ions. The distance between the ion inlet orifice and the ion outlet orifice is also smaller, and may result in insufficient ion transit times to effect separation of a mixture that contains different ionic species having similar high field ion mobility properties.

It would be advantageous to provide a FAIMS apparatus including a detection system that overcomes the limitations of the prior art.

SUMMARY OF THE INVENTION

In accordance with an aspect of the invention there is provided an apparatus for separating ions, comprising: an outer electrode comprising an inner curved electrode surface defining an internal cavity, an inlet through a first portion of the inner curved electrode surface for introducing ions and a flow of a carrier gas into an inlet region of the internal cavity proximate the inlet, and an outlet through a second portion of the inner curved electrode surface for extracting ions from an outlet region of the internal cavity proximate the outlet; an inner electrode comprising an outer curved electrode surface, the inner electrode disposed within the internal cavity in a spaced apart arrangement with the outer electrode, the space between the inner electrode and the outer electrode defining an analyzer region extending between the inlet region and the outlet region; and, an electrical contact on at least one of the outer electrode and the inner electrode for applying a compensation voltage between the outer electrode and the inner electrode, and for applying an asymmetric waveform to the at least one of the outer electrode and the inner electrode such that, during use, some of the ions are selectively transmitted through the analyzer region between the inlet region and the outlet region along at least three different approximately shortest average ion flow paths that are other than parallel one relative to another along a substantial portion of a length thereof.

In accordance with another aspect of the invention there is provided an apparatus for separating ions, comprising: an outer electrode comprising an inner curved electrode surface defining an approximately elliptical cavity; an approximately ellipsoid inner electrode disposed within the approximately elliptical cavity; a support member in communication with the inner electrode for supporting the inner electrode in a spaced apart arrangement with the outer electrode such that an approximately same distance is maintained between the inner electrode and the outer electrode at every point along the surface of the inner electrode other than proximate the support member; and, an electrical contact on at least one of the outer electrode and the inner electrode for applying a compensation voltage between the outer electrode and the inner electrode, and for applying an asymmetric waveform voltage to the at least one of the outer electrode and the inner electrode.

BRIEF DESCRIPTION OF THE DRAWINGS

Exemplary embodiments of the invention will now be described in conjunction with the following drawings, in which similar reference numbers designate similar items:

FIG. 1b is a side elevational view of the cylindrical side-to-side FAIMS device shown in FIG. 1a;

DETAILED DESCRIPTION OF THE DRAWINGS

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1A:
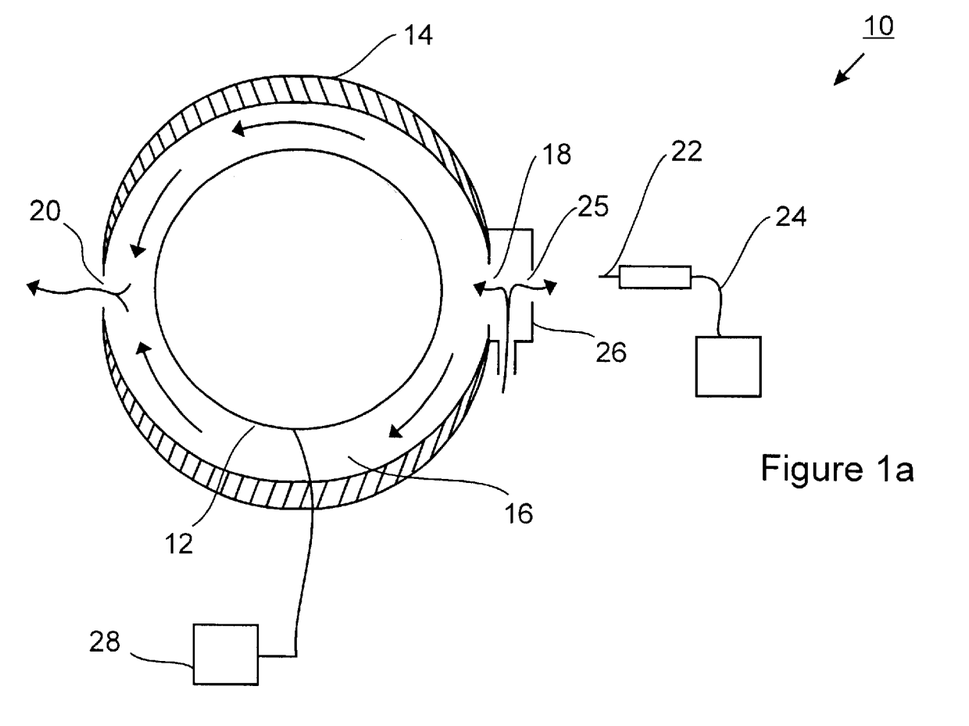
FIG. 1a is a simplified cross sectional view of a cylindrical side-to-side FAIMS device.

Referring to FIG. 1a, shown is a simplified cross sectional view of a cylindrical side-to-side FAIMS. The cylindrical side-to-side FAIMS device, shown generally at 10, includes inner and outer cylindrical electrodes 12 and 14, respectively, which are supported by an electrically insulating material (not shown) in an overlapping, spaced-apart arrangement. The generally annular space between the inner electrode 12 and the outer electrode 14 defines a FAIMS analyzer region 16. The analyzer region 16 is of approximately uniform width and extends around the circumference of the inner electrode 12. An ion inlet orifice 18 is provided through the outer electrode 14 for introducing ions from an ion source into the analyzer region 16. For example, the ion source is in the form of an electrospray ionization ion source including a liquid delivery capillary 24, a fine-tipped electrospray needle 22 that is held at high voltage (power supply not shown) and a curtain plate 26 serving as a counter-electrode for the electrospray needle 22. Of course, any other suitable ionization source is used optionally in place of the electrospray ionization ion source. A flow of a carrier gas, which is represented in the figure by a series of closed-headed arrows, is provided within the analyzer region 16 to carry the ions around the inner electrode 12 and toward an ion outlet orifice 20. An orifice 25 within the curtain plate electrode 26 allows for the flow of a portion of the carrier gas in a direction that is counter-current to the direction in which the ions are traveling near the ion inlet orifice 18, so as to desolvate the ions before they are introduced into the analyzer region 16. The inner electrode 12 is in electrical communication with a power supply 28 that during use is capable of applying a high voltage asymmetric waveform voltage (DV) and a low voltage dc compensation voltage (CV) to the inner FAIMS electrode 12.

Still referring to FIG. 1a, ions are produced in the gas phase at the fine-tipped electrospray needle 22 from a suitable sample containing a species of interest. Typically, a mixture including a plurality of different ion types is produced when the sample is ionized. A potential gradient is used to accelerate the ions of the mixture away from the electrospray needle 22, through the orifice 25 in the curtain plate electrode 26, and toward the ion inlet orifice 18, where the ions become entrained in the carrier gas flow and are carried into the FAIMS analyzer region 16. Once inside the FAIMS analyzer region 16, the ions are carried through an electric field that is formed within the FAIMS analyzer region 16 by the application of the DV and the CV to the inner FAIMS electrode 12. Ion separation occurs within the FAIMS analyzer region 16 on the basis of the high field mobility properties of the ions. Those ions of the mixture that have a stable trajectory for a particular combination of DV and CV are selectively transmitted through the FAIMS analyzer region 16, whilst other ions of the mixture collide with an electrode surface and are lost. The selectively transmitted ions are extracted from the analyzer region 16 via ion outlet orifice 20 and are typically subjected to one of detection and further analysis.

Figure 1B:
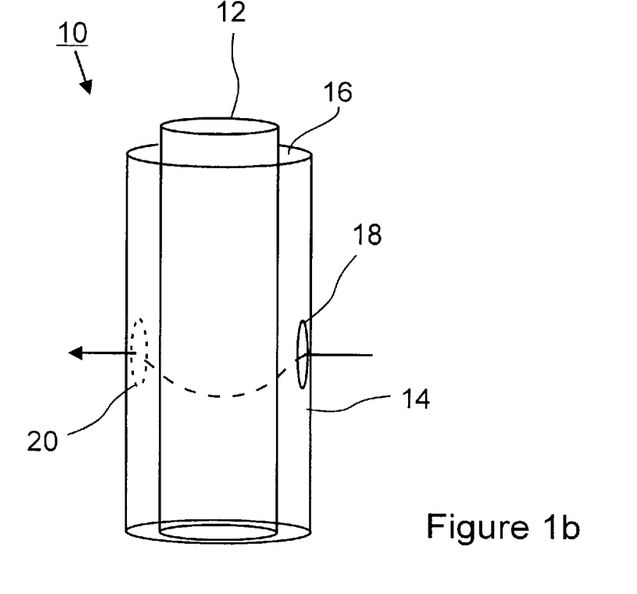

Referring now to FIG. 1b, shown is a simplified side elevational view of the cylindrical side-to-side FAIMS of FIG. 1a. Elements labeled with the same numerals have the same function as those illustrated in FIG. 1a. The dotted line extending between ion inlet 18 and ion outlet 20 represents one possible average ion flow path around the inner electrode 12. An average ion flow path is defined as the net trajectory of an ion as a result of a carrier gas flow through the analyzer region, although the individual ion also experiences an oscillatory motion between the electrodes as a result of the applied asymmetric waveform voltage. In particular, the dotted line represents one of two shortest average ion flow paths through the analyzer region 16, one shortest average ion flow path extending in each direction around the inner electrode 12. Of course, when many like-charged ions are present within the analyzer region, ion-ion repulsion forces tend to cause the ions to spread out slightly along the length of the inner electrode 12. Accordingly, some ions are selectively transmitted through the analyzer region 16 along other average ion flow paths that are longer than the one illustrated in FIG. 1b. Furthermore, some selectively transmitted ions migrate into portions of the analyzer region where the gas flow rate is low or stagnant, making their extraction from the analyzer region difficult. It is a disadvantage of the cylindrical side-to-side FAIMS that ions introduced into the analyzer region 16 during a same period of time are subjected to different conditions during selective transmission to the ion outlet. As a result, the extent to which a mixture of ions is separated becomes a complex function of the various paths that the ions follow through the analyzer region 16.

Figure 2A:
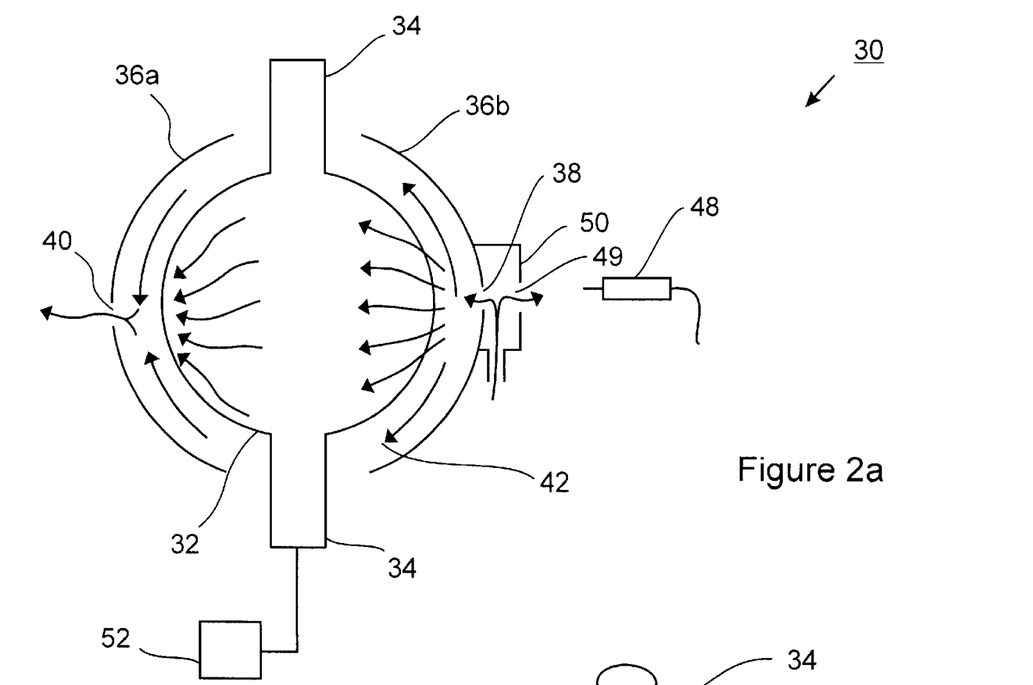
FIG. 2a is a side view of a spherical side-to-side FAIMS device.

Referring now to FIG. 2a, shown is a side view of a spherical side-to-side FAIMS device according to the instant invention. The spherical side-to-side FAIMS, shown generally at 30, includes an inner electrode 32 having a spherical shape with the exception of two rod-like protrusions 34 for supporting the inner electrode 32 in place. For example, each one of the two rod-like protrusions 34 is embedded within a PEEK insulator material (not shown). A two-piece outer electrode 36a, 36b forms a spherical shell that surrounds the inner electrode 32 in a spaced-apart arrangement. Of course, the two-piece outer electrode 36a, 36b is preferably held in place relative to the inner electrode by an electrically insulating material (not shown). The space between the inner electrode 32 and the two-piece outer electrode 36a, 36b defines a FAIMS analyzer region 42. The analyzer region 42 is of approximately uniform width and extends all the way around the outer surface of the inner electrode 32 between an ion inlet orifice 38 and an ion outlet orifice 40. The ion inlet orifice 38 is provided through the outer electrode 36b for receiving ions from an ion source for introduction into the analyzer region 42. For example, the ion source is in the form of an electrospray ionization ion source 48 and a curtain plate electrode 50. Of course, any other suitable ionization source is used optionally in place of the electrospray ionization ion source. A flow of a carrier gas, which is represented in the figure by a series of closed-headed arrows, is provided within the analyzer region 42 to carry the ions around the inner electrode 32 and toward the ion outlet orifice 40. An orifice 49 within the curtain plate electrode 50 allows for the flow of a portion of the carrier gas in a direction that is counter-current to the direction in which the ions are traveling near the ion inlet 38, so as to desolvate the ions before they are introduced into the analyzer region 42. The inner electrode 32 is in electrical communication with a power supply 52 that during use is capable of applying a high voltage asymmetric waveform voltage (DV) and a low voltage dc compensation voltage (CV) to the inner FAIMS electrode 32.

During use, ions are produced in the gas phase for introduction into spherical side-to-side FAIMS 30 from a suitable sample containing a species of interest. Typically, a mixture including a plurality of different ion types is produced when the sample is ionized. A potential gradient is used to accelerate the ions of the mixture away from the electrospray ion source 48, through the orifice 49 in the curtain plate electrode 50, and toward the ion inlet orifice 38, where the ions become entrained in the carrier gas flow and are carried into the FAIMS analyzer region 42. Once inside the FAIMS analyzer region 42, the ions are carried through an electric field that is formed within the FAIMS analyzer region 42 by the application of the DV and the CV to the inner FAIMS electrode 32. Ion separation occurs within the FAIMS analyzer region 42 on the basis of the high field mobility properties of the ions. Those ions of the mixture that have a stable trajectory for a particular combination of DV and CV are selectively transmitted through the FAIMS analyzer region 42, whilst other ions of the mixture collide with an electrode surface and are lost. The selectively transmitted ions are extracted from the analyzer region 42 via ion outlet orifice 40 and are typically subjected to one of detection and further analysis.

Figure 2B:
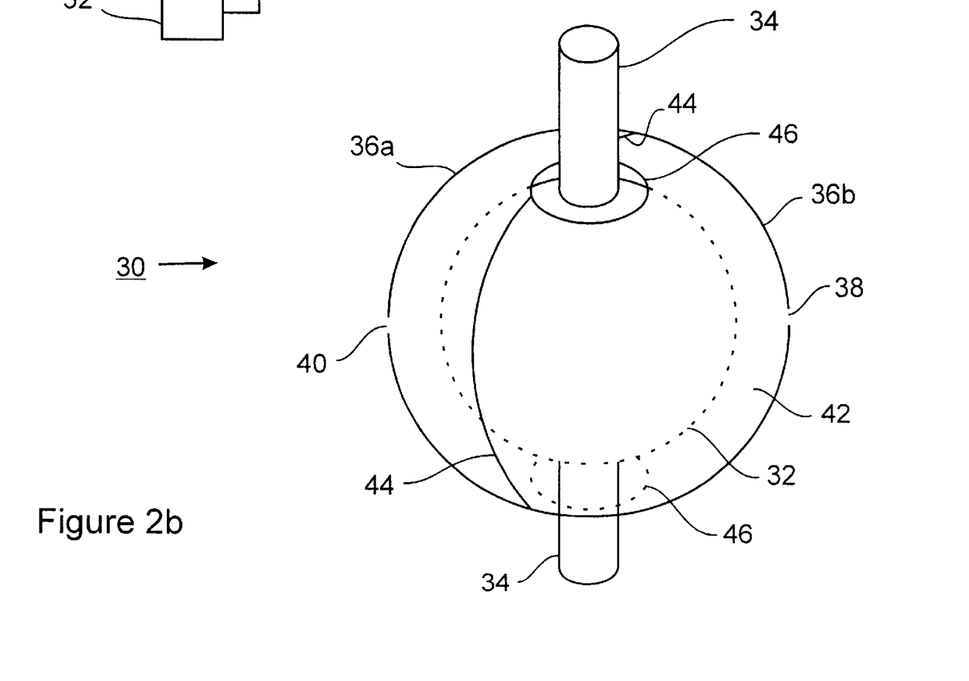
FIG. 2b is a side elevational view of a spherical side-to-side FAIMS device.

Referring now to FIG. 2b, shown is a side elevational view of a spherical side-to-side FAIMS device. Elements labeled with the same numerals have the same function as those illustrated in FIG. 2a. The side elevational view of the spherical side-to-side FAIMS 30 shows more clearly the structure of the two-piece outer electrode, including the first outer electrode portion 36a and the second outer electrode portion 36b. When in the assembled condition as illustrated in FIG. 2b, the two outer electrode portions 36a and 36b are closely fitted together and form a seam 44 where the two portions meet. Advantageously, the inner electrode 32 can be inserted within the two outer electrode portions 36a and 36b during assembly, such that each one of the two rod-like protrusions 34 extends radially outwardly through an opening 46 in the two-piece outer electrode 36a, 36b.

Figure 3:
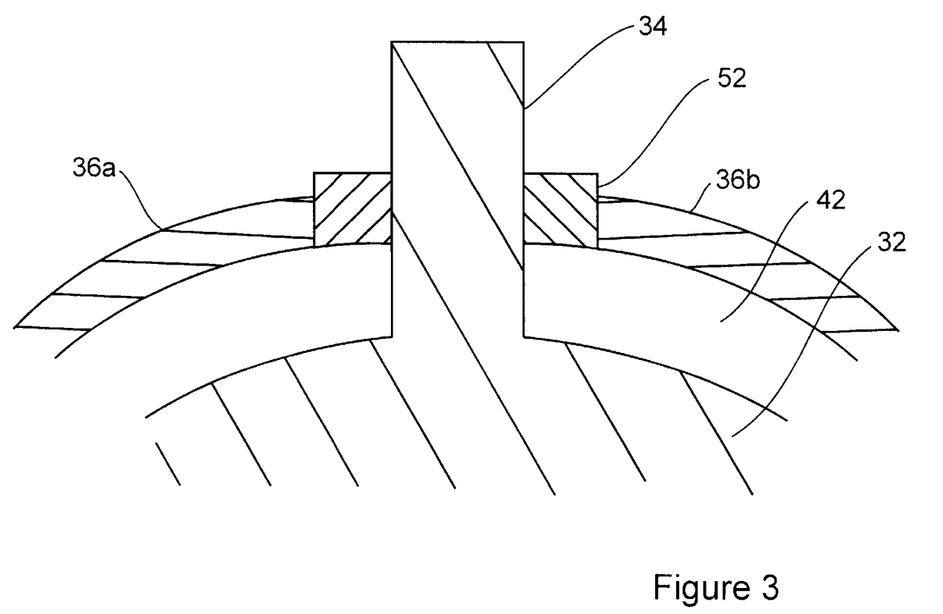
FIG. 3 is a partial enlarged view of the spherical side-to-side FAIMS device.

Referring now to FIG. 3, shown is an enlarged view illustrating a gas tight seal between the rod-like protrusions 34 and the two-piece outer electrode 36a, 36b. In particular, the rod-like protrusion 34 is fitted with a ring 52 of an insulating material, the ring 52 having an opening that is sized to accommodate the rod-like protrusion 34 therein. The ring 52 is also sized to provide a gas-tight fit with the two-piece outer electrode 36a, 36b when the spherical side-to-side FAIMS device is in the assembled condition. Preferably, the ring 52 is formed of a single piece of insulating material. Optionally, the ring 52 is formed of at least two separate pieces that cooperate to form a gas tight seal between the rod-like protrusion 34 and the two-piece outer electrode 36a, 36b when the spherical side-to-side FAIMS device is in the assembled condition.

Optionally, the rod-like protrusions 34 are made of PEEK and extend from outside of the outer electrode down into the conductive inner electrode. The presence of this insulating material will modify the electric fields in the vicinity of the PEEK between the inner and outer electrode because of the electric charges that accumulate from ions that collide with the insulator.

Unlike the cylindrical side-to-side FAIMS described supra, in which the electric field varies in the radial direction as a function of 1/r, where r is the radial location taking r=0 at the center of rotational symmetry, the electric fields of the spherical side-to-side FAIMS vary as a function of $1/r^2$, again taking r=0 at the center of spherical symmetry. These changes in electric field as a function of radius result in improved focusing capabilities, for instance a stronger focusing effect, which improves the performance of the spherical side-to-side FAIMS device relative to that of the cylindrical side-to-side FAIMS.

In addition, the geometry of the spherical shape is advantageous compared with the prior art cylindrical shape in that the gas flows converging towards the ion outlet act to direct the ions towards the ion outlet much like the hemispherical terminus in the domed-FAIMS device. The gas flow entering the ion inlet travel equal distances regardless of the direction of the flow path that is taken to the ion outlet, therefore the gas radiates in every direction away from the ion inlet. Similarly, the gas flow converges from every direction toward the ion outlet. Advantageously, the gas velocity is approximately equal along every flow path, and there are no regions of stagnant gas within the spherical analyzer region 42. However, the gas velocity is higher near the ion inlet 38 and outlet 40 than it is at a point equidistant from the ion inlet 38 and ion outlet 40.

It is a further advantage of the spherical side-to-side FAIMS that the ions travel through the analyzer region along more than two approximately shortest average ion flow paths, where the term "average ion flow path" is defined as the net trajectory of an ion as a result of a carrier gas flow through the analyzer region, although the individual ion also experiences an oscillatory motion between the electrodes as a result of the applied asymmetric waveform voltage. Accordingly, an approximately shortest average ion flow path is defined as a net ion trajectory that curves continuously in one direction only and that extends between an inlet region proximate the ion inlet orifice 38 and an outlet region proximate the ion outlet orifice 40. As discussed supra the gas flow entering the ion inlet travels equal distances between the ion inlet and the ion outlet, regardless of the direction of the path that is taken. Accordingly, the gas radiates equally in every direction away from the ion inlet. Since the ions are entrained within the gas flow, the ions also radiate equally in every direction away from the ion inlet, travelling an approximately equal distance to the ion outlet. Since every ion travels an approximately equal distance to the ion outlet, every average ion flow path is an approximately shortest average ion flow path through the analyzer region of the spherical side-to-side FAIMS. It is a further advantage of the spherical side-to-side FAIMS that ions introduced into the analyzer region 42 during a same period of time are subjected to approximately identical conditions during selective transmission to the ion outlet. As a result, the extent to which a mixture of ions is separated becomes approximately independent of the path taken through the analyzer region 42. Clearly, however, those ions that are carried toward the rod-like protrusions 34 may be lost if the electric field strength changes in the vicinity of these protrusions. Such ions are lost if the electric fields created by the applied experimental conditions, including DV and CV, fail to produce a 'virtual' potential well or ion focusing region for this ion that is continuous near these posts in such a way as to minimize ion loss. If the 'virtual' potential well doesn't exist, or it ends on a conductive surface, an ion loss to this surface through diffusion and space charge repulsion will occur.

Furthermore, the ion density becomes spread out more uniformly around the inner electrode of the spherical side-to-side FAIMS than is possible within a cylindrical side-to-side FAIMS. This is because the gas flow, which carries the ions through the analyzer region 42, radiates equally in every direction away from the ion inlet and around the inner electrode 32. As discussed with reference to FIGS. 1a and 1b, the ions are forced to travel around the cylindrical inner electrode 12 in one of a "clock-wise" and a "counter clock-wise" direction, with approximately one half of the ions traveling in each direction. In the cylindrical geometry case, the ion density tends to remain relatively high along an axis defined between the ion inlet orifice 18 and the ion outlet orifice 20. Diffusion and ion-ion repulsive forces cause some of the ions to spread out non-uniformly along the length of the inner electrode 12. For instance, the extent to which the ions spreads out is greater near the ion outlet orifice 20 since the ions require time in order to move away from a central region of the analyzer. In this case, the central region of the analyzer region is defined as a portion of the analyzer region 42 extending directly between the ion inlet orifice and the ion outlet orifice. Of course, the ion density profile in either direction away from the central region of the analyzer decreases continuously. As a result, the ions are spread out non-uniformly in the cylindrical side-to-side FAIMS device.

Figure 2C:
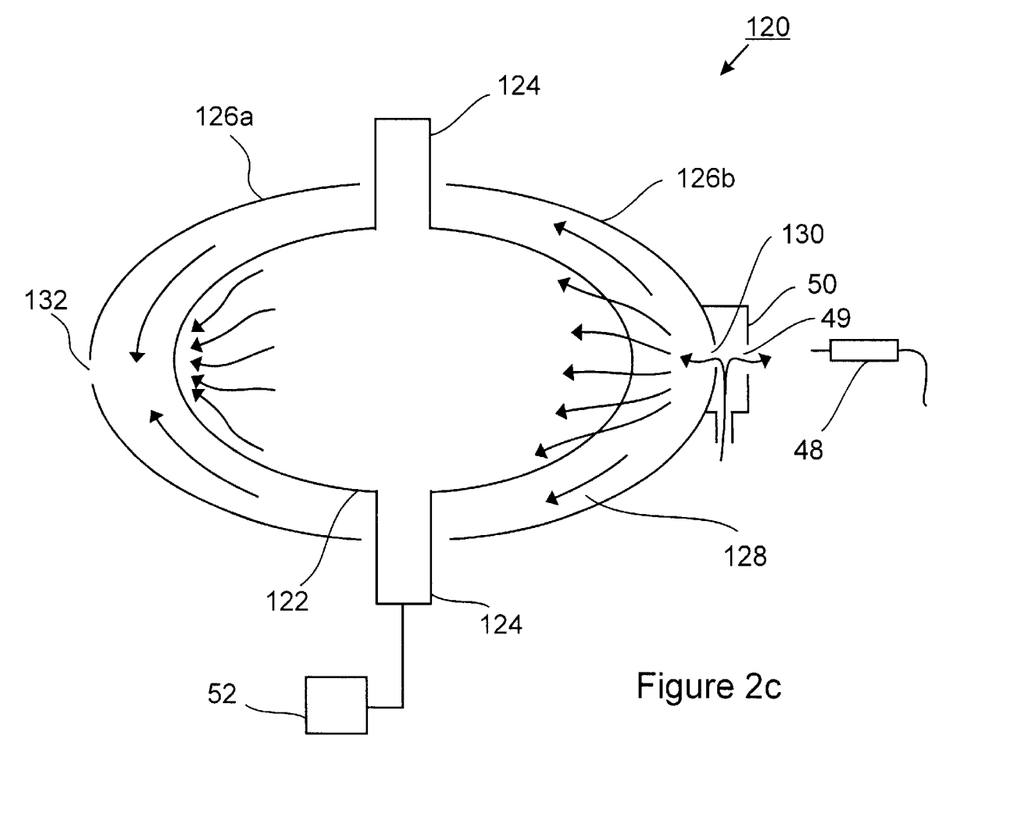
FIG. 2c is a side view of a modified spherical side-to-side FAIMS device.

Of course, the spherical shape of the inner electrode may be varied without departing from the spirit and scope of the instant invention. In particular, the embodiment described with reference to FIG. 2a represents a specific example of a FAIMS device having an ellipsoid inner electrode in which the minor axis and the major axis are approximately identical. Referring now to FIG. 2c, shown is a modified spherical side-to-side FAIMS device 120 including an inner electrode 122 having an ellipsoid shape with the exception of two rod-like protrusions 124 for supporting the inner electrode 122 in place. In particular, the inner electrode 122 is provided as a prolate ellipsoid having a major axis longer than a minor axis thereof. Each one of the two rod-like protrusions 124 is embedded within a PEEK insulator material (not shown). A two-piece outer electrode 126a, 126b forms a shell that surrounds the inner electrode 122 in a spaced-apart arrangement. Of course, the two-piece outer electrode 126a, 126b is preferably held in place relative to the inner electrode by an electrically insulating material (not shown). The space between the inner electrode 122 and the two-piece outer electrode 126a, 126b defines a FAIMS analyzer region 128. The analyzer region 128 is of approximately uniform width and extends all the way around the outer surface of the inner electrode 122 between an ion inlet orifice 130 and an ion outlet orifice 132. The ion inlet orifice 130 is provided through the outer electrode 126b for receiving ions from an ion source for introduction into the analyzer region 128. For example, the ion source is in the form of an electrospray ionization ion source 48. Of course, any other suitable ionization source is used optionally in place of the electrospray ionization ion source. A flow of a carrier gas, which is represented in the figure by a series of closed-headed arrows, is provided within the analyzer region 128 to carry the ions around the inner electrode 122 and toward the ion outlet orifice 132. An orifice 49 within a curtain plate electrode 50 allows for the flow of a portion of the carrier gas in a direction that is counter-current to the direction in which the ions are traveling near the ion inlet 130, so as to desolvate the ions before they are introduced into the analyzer region 128. The inner electrode 122 is in electrical communication with a power supply 52 that during use is capable of applying a high voltage asymmetric waveform voltage (DV) and a low voltage dc compensation voltage (CV) to the inner FAIMS electrode 122.

Since the radius of curvature of the prolate ellipsoid shaped inner electrode 122 is approximately identical proximate both at the ion inlet end and at the ion outlet end, so too are the electric fields in the vicinity of the ion inlet orifice 130 and the ion outlet orifice 132 approximately identical. A prolate ellipsoid shaped inner electrode, as described with reference to FIG. 2c, produces many of the same advantages as were described with reference to the spherical shaped electrode.

Figure 4:
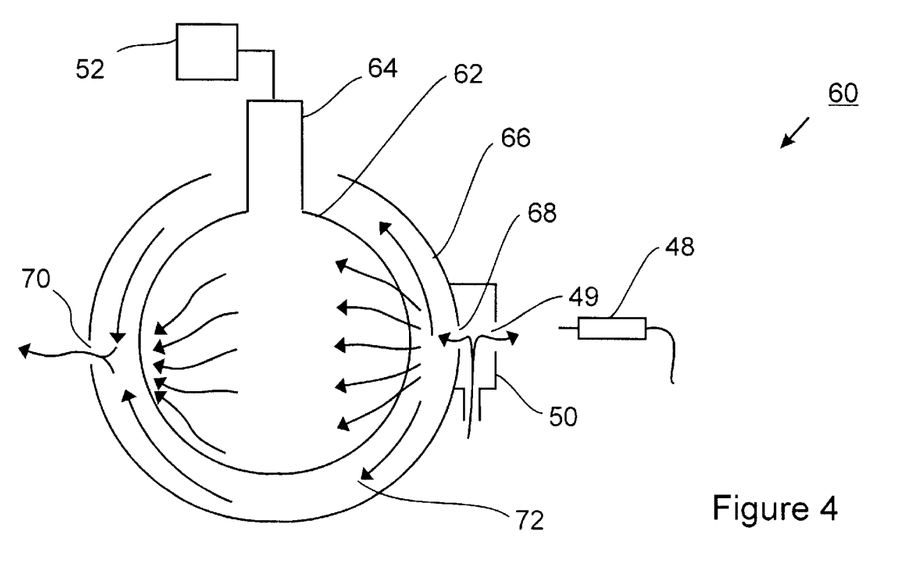
FIG. 4 is a side view of a second spherical side-to-side FAIMS device.

Referring now to FIG. 4, shown is a side view of a second spherical side-to-side FAIMS device. Elements labeled with the same numerals have the same function as those illustrated in FIG. 2a. The spherical side-to-side FAIMS, shown generally at 60, includes an inner electrode 62 having a spherical shape with the exception of one rod-like protrusion 64 for supporting the inner electrode 62 in place. A one-piece outer electrode 66 forms a spherical shell that surrounds the inner electrode 62 in a spaced-apart arrangement. The space between the inner electrode 62 and the one-piece outer electrode 66 defines a FAIMS analyzer region 72. The analyzer region 72 is of approximately uniform width and extends all the way around the outer surface of the inner electrode 62 between an ion inlet orifice 68 and an ion outlet orifice 70. The ion inlet orifice 68 is provided through the outer electrode 66 for receiving ions from an ion source for introduction into the analyzer region 72. For example, the ion source is in the form of an electrospray ionization ion source 48. Of course, any other suitable ionization source is used optionally in place of the electrospray ionization ion source. A flow of a carrier gas, which is represented in the figure by a series of closed-headed arrows, is provided within the analyzer region 72 to carry the ions around the inner electrode 62 and toward the ion outlet orifice 70. An orifice 49 within a curtain plate electrode 50 allows for the flow of a portion of the carrier gas in a direction that is counter-current to the direction in which the ions are traveling near the ion inlet 68, so as to desolvate the ions before they are introduced into the analyzer region 72. The inner electrode 62 is in electrical communication with a power supply 52 that during use is capable of applying a high voltage asymmetric waveform voltage (DV) and a low voltage dc compensation voltage (CV) to the inner FAIMS electrode 62.

During use, ions are produced in the gas phase for introduction into spherical side-to-side FAIMS 60 from a suitable sample containing a species of interest. Typically, a mixture including a plurality of different ion types is produced when the sample is ionized. A potential gradient is used to accelerate the ions of the mixture away from the electrospray ion source 48, through the orifice 49 in the curtain plate electrode 50, and toward the ion inlet orifice 68, where the ions become entrained in the carrier gas flow and are carried into the FAIMS analyzer region 72. Once inside the FAIMS analyzer region 72, the ions are carried through an electric field that is formed within the FAIMS analyzer region 72 by the application of the DV and the CV to the inner FAIMS electrode 62. Ion separation occurs within the FAIMS analyzer region 72 on the basis of the high field mobility properties of the ions. Those ions of the mixture that have a stable trajectory for a particular combination of DV and CV are selectively transmitted through the FAIMS analyzer region 72, whilst other ions of the mixture collide with an electrode surface and are lost. Advantageously, the analyzer region 72 of FAIMS 60 is interrupted in the vicinity of only one rod-like protrusion 64, in contrast to the spherical side-to-side FAIMS 30 of FIG. 2a in which two such interruptions are created, one in the vicinity of each rod-like protrusion 34.

The one-piece electrode 66 is preferably formed around the inner electrode 62, for example by constructing initially a polymer based electrode support using the application of laser light to solidify the polymer material as is done in stereolithography (SLA). The polymer based electrode support is built up around the inner electrode, eventually completely encircling the inner electrode except over a region thereof proximate the one rod-like protrusion 64. Subsequently, a layer of a conductive material is deposited onto an inner surface of the polymer based electrode support. Optionally, a two-piece outer electrode including two hemispherical halves is used, as was described with reference to FIG. 2a.

Figure 5A:
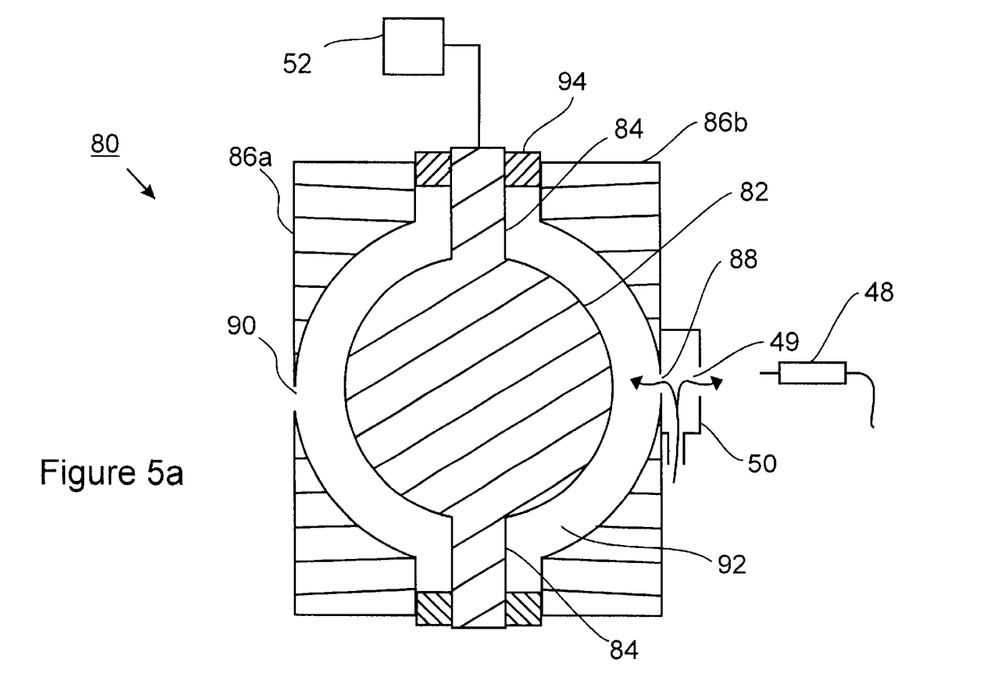
FIG. 5a is a side view of a third spherical side-to-side FAIMS device.

Referring now to FIG. 5a, shown is a side view of a third spherical side-to-side FAIMS device. Elements labeled with the same numerals have the same function as those illustrated in FIG. 2a. The spherical side-to-side FAIMS, shown generally at 80, includes an inner electrode 82 having a spherical shape with the exception of two rod-like protrusions 84 for supporting the inner electrode 82 in place. A two-piece outer electrode 86a, 86b forms a spherical shell that surrounds the inner electrode 82 in a spaced-apart arrangement. The space between the inner electrode 82 and the two-piece outer electrode 86a, 86b defines a FAIMS analyzer region 92. The analyzer region 92 is of approximately uniform width and extends all the way around the outer surface of the inner electrode 82 between an ion inlet orifice 88 and an ion outlet orifice 90. The ion inlet orifice 88 is provided through the outer electrode 86b for receiving ions from an ion source for introduction into the analyzer region 92. For example, the ion source is in the form of an electrospray ionization ion source 48. Of course, any other suitable ionization source is used optionally in place of the electrospray ionization ion source. A flow of a carrier gas, which is represented in the figure by a series of closed-headed arrows, is provided within the analyzer region 92 to carry the ions around the inner electrode 82 and toward the ion outlet orifice 90. An orifice 49 within a curtain plate electrode 50 allows for the flow of a portion of the carrier gas in a direction that is counter-current to the direction in which the ions are traveling near the ion inlet 88, so as to desolvate the ions before they are introduced into the analyzer region 92. The inner electrode 82 is in electrical communication with a power supply 52 that during use is capable of applying a high voltage asymmetric waveform voltage (DV) and a low voltage dc compensation voltage (CV) to the inner FAIMS electrode 82. A ring 94 that is formed of an electrically insulating material is fitted around the rod-like protrusions 84 for providing a gas-tight seal with the two-piece outer electrode 86a, 86b.

During use, ions are produced in the gas phase for introduction into spherical side-to-side FAIMS 80 from a suitable sample containing a species of interest. Typically, a mixture including a plurality of different ion types is produced when the sample is ionized. A potential gradient is used to accelerate the ions of the mixture away from the electrospray ion source 48, through the orifice 49 in the curtain plate electrode 50, and toward the ion inlet orifice 88, where the ions become entrained in the carrier gas flow and are carried into the FAIMS analyzer region 92. Once inside the FAIMS analyzer region 92, the ions are carried through an electric field that is formed within the FAIMS analyzer region 92 by the application of the DV and the CV to the inner FAIMS electrode 82. Ion separation occurs within the FAIMS analyzer region 92 on the basis of the high field mobility properties of the ions. Those ions of the mixture that have a stable trajectory for a particular combination of DV and CV are selectively transmitted through the FAIMS analyzer region 92, whilst other ions of the mixture collide with an electrode surface and are lost.

Figure 5B:
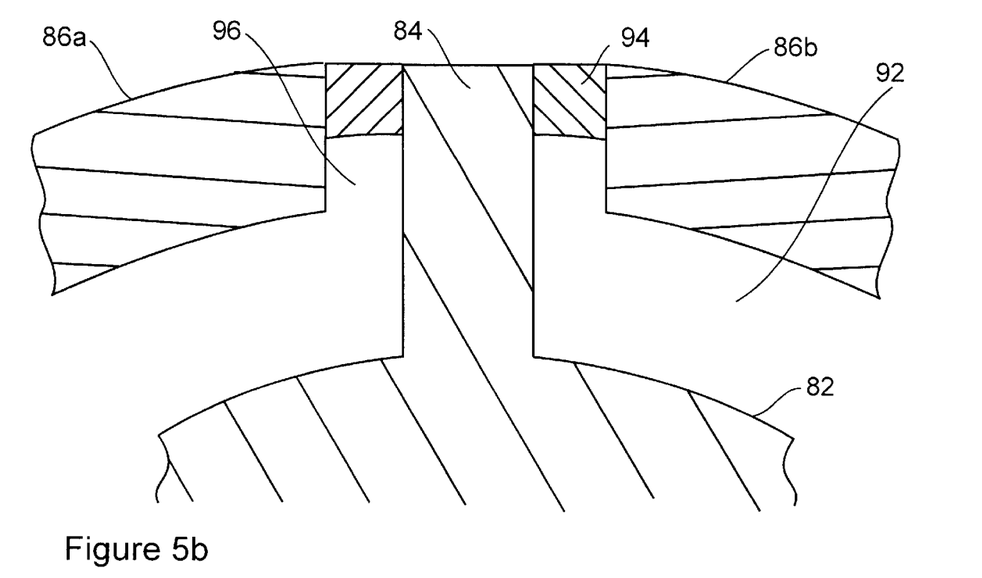
FIG. 5b is a partial enlarged view of the third spherical side-to-side FAIMS device; and, FIG. 6 is a side elevational view of a modified spherical side-to-side FAIMS device.

Referring now to FIG. 5b, shown is an enlarged view illustrating a gas tight seal between the rod-like protrusions 84 and the two-piece outer electrode 86a, 86b. Each rod-like protrusion 84 extends radially outwardly through an opening 96 in the two-piece outer electrode 86a, 86b. The ring 94 is disposed within opening 96 and forms a gas tight seal with the two-piece outer electrode 86a, 86b. Preferably, the ring 94 includes a first surface facing inwardly towards the analyzer region 82, which first surface is recessed within the opening 96. Since the ring 94 is constructed from an electrically insulating material, ions colliding therewith cause a charge buildup that affects the electric field within the analyzer region due to the applied DV and the applied CV. The effect of such a charge buildup is expected to diminish when the ring 94 is recessed relative to the inner surfaces of the two-piece outer electrode 86a, 86b.

Figure 6:
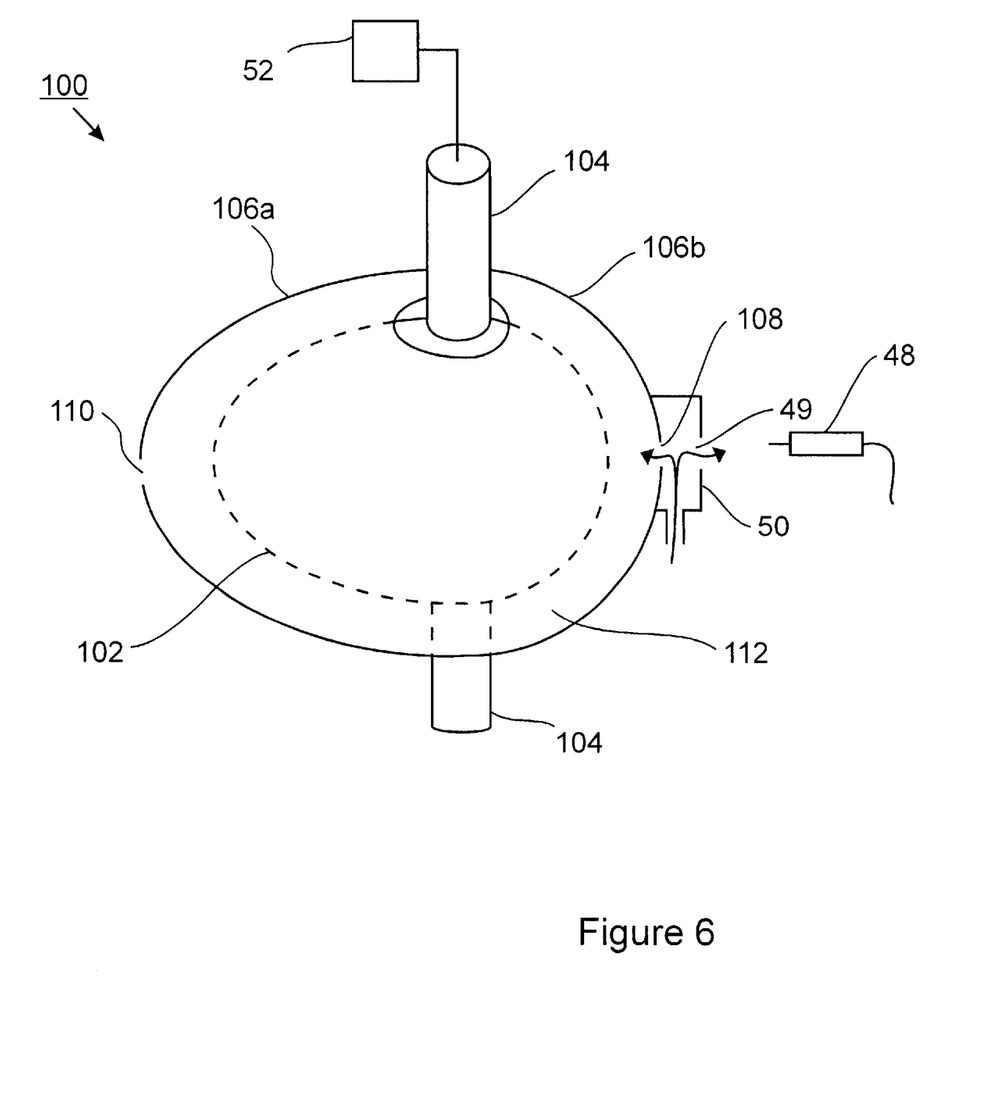

Referring now to FIG. 6, shown is a side elevational view of a modified ellipsoid side-to-side FAIMS device. Elements labeled with the same numerals have the same function as those illustrated in FIG. 2a. The spherical side-to-side FAIMS, shown generally at 100, includes a generally egg-shaped inner electrode 102 having two rod-like protrusions 104 for supporting the inner electrode 102 in place. For example, each one of the two rod-like protrusions 104 is embedded within a PEEK insulator material (not shown). A two-piece outer electrode 106a, 106b forms a shell that surrounds the inner electrode 102 in a spaced-apart arrangement. Of course, the two-piece outer electrode 106a, 106b is preferably held in place relative to the inner electrode by an electrically insulating material (not shown). The space between the inner electrode 102 and the two-piece outer electrode 106a, 106b defines a FAIMS analyzer region 112. The analyzer region 112 is of approximately uniform width and extends all the way around the outer surface of the inner electrode 102 between an ion inlet orifice 108 and an ion outlet orifice 110. The ion inlet orifice 108 is provided through the outer electrode 106b for receiving ions from an ion source for introduction into the analyzer region 112. For example, the ion source is in the form of an electrospray ionization ion source 48. Of course, any other suitable ionization source is used optionally in place of the electrospray ionization ion source. A flow of a carrier gas, which is represented in the figure by a series of closed-headed arrows, is provided within the analyzer region 112 to carry the ions around the inner electrode 102 and toward the ion outlet orifice 110. An orifice 49 within a curtain plate electrode 50 allows for the flow of a portion of the carrier gas in a direction that is counter-current to the direction in which the ions are traveling near the ion inlet 108, so as to desolvate the ions before they are introduced into the analyzer region 112. The inner electrode 102 is in electrical communication with a power supply 52 that during use is capable of applying a high voltage asymmetric waveform voltage (DV) and a low voltage dc compensation voltage (CV) to the inner FAIMS electrode 102.

During use, ions are produced in the gas phase for introduction into the modified ellipsoid side-to-side FAIMS 100 from a suitable sample containing a species of interest. Typically, a mixture including a plurality of different ion types is produced when the sample is ionized. A potential gradient is used to accelerate the ions of the mixture away from the electrospray ion source 48, through the orifice 49 in the curtain plate electrode 50, and toward the ion inlet orifice 108, where the ions become entrained in the carrier gas flow and are carried into the FAIMS analyzer region 112. Once inside the FAIMS analyzer region 112, the ions are carried through an electric field that is formed within the FAIMS analyzer region 112 by the application of the DV and the CV to the inner FAIMS electrode 102. Ion separation occurs within the FAIMS analyzer region 112 on the basis of the high field mobility properties of the ions. Those ions of the mixture that have a stable trajectory for a particular combination of DV and CV are selectively transmitted through the FAIMS analyzer region 112, whilst other ions of the mixture collide with an electrode surface and are lost.

In the modified ellipsoid side-to-side FAIMS device 100, the electric fields are different at the ion inlet region and at the ion outlet region. For example, the radius of curvature of the surface of the inner electrode 102 in the vicinity of the ion inlet orifice 108 is larger than the radius of curvature of the inner electrode 102 in the vicinity of the ion outlet orifice 110. Accordingly, stronger focusing fields are created proximate the ion outlet orifice 110, which improves extraction efficiency from the analyzer region 112. This is in contrast to the FAIMS device 120 described with reference to FIG. 2c in which the electric fields are approximately identical at the ion inlet region and at the ion outlet region.

Although the CV and DV are shown being applied to the inner electrode in the above drawings, optionally the CV and the DV are applied one each to a different electrode. Further optionally, both the CV and the DV are applied to the outer electrode.

Further optionally, the inner electrodes that are described with reference to FIGS. 2a through 6 are one of a solid electrode formed of a single conductive material, a solid electrode formed of a first material and having a layer of a conductive second material deposited thereon, and a hollow electrode having an outer surface formed of a conductive material.

Numerous other embodiments may be envisaged without departing from the spirit and scope of the invention.

What is claimed is:

1. An apparatus for separating ions, comprising:
    an outer electrode comprising an inner curved electrode surface defined by a curve rotated about a central axis and defining an internal cavity, an inlet through a first portion of the inner curved electrode surface for introducing ions and a flow of a carrier gas into an inlet region of the internal cavity proximate the inlet, and an outlet through a second portion of the inner curved electrode surface for extracting ions from an outlet region of the internal cavity proximate the outlet;
    an inner electrode comprising an outer curved electrode surface, the inner electrode disposed within the internal cavity in a spaced apart arrangement with the outer electrode, the space between the inner electrode and the outer electrode defining an analyzer region extending between the inlet region and the outlet region; and,
    an electrical contact on at least one of the outer electrode and the inner electrode for applying a compensation voltage between the outer electrode and the inner electrode, and for applying an asymmetric waveform to the at least one of the outer electrode and the inner electrode such that, during use, some of the ions are selectively transmitted through the analyzer region between the inlet region and the outlet region along at least three different approximately shortest average ion flow paths that are other than parallel, one relative to another, along a substantial portion of a length thereof.

2. An apparatus according to claim 1, wherein the at least three different approximately shortest average ion flow paths are approximately radially symmetric about a line formed approximately between the inlet region and the outlet region.

3. An apparatus according to claim 1, wherein ions flowing along each one of the at least three different approximately shortest average ion flow paths travel an approximately same distance between the inlet region and the outlet region.

4. An apparatus according to claim 1, wherein the outer curved electrode surface has an approximately same surface profile taken along every direction within a portion thereof proximate the inlet region.

5. An apparatus according to claim 1, wherein the outer curved electrode surface defines an ellipsoid surface.

6. An apparatus according to claim 5, wherein the ellipsoid surface is approximately spherically shaped.

7. An apparatus according to claim 1, wherein, during use, a similar electric field is formed at the inlet region and at the outlet region.

8. An apparatus according to claim 1, wherein the outer electrode comprises a first outer electrode portion including a first inner curved electrode surface portion and a second outer electrode portion including a second inner curved electrode surface portion that is approximately contiguous with the first inner curved electrode surface portion.

9. An apparatus according to claim 1, wherein the inner electrode includes a support post extending outward therefrom and passing through an opening in the inner curved electrode surface of the outer electrode.

10. An apparatus according to claim 9, comprising an electrically insulating material disposed between the support post and the outer electrode.

11. An apparatus according to claim 10, wherein the electrically insulating material forms a gas tight seal between the support post and the outer electrode.

12. An apparatus for separating ions, comprising:

an outer electrode comprising an inner curved electrode surface defining an approximately elliptical cavity;

an approximately ellipsoid inner electrode disposed within the approximately elliptical cavity;

a support member in communication with the inner electrode for supporting the inner electrode in a spaced apart arrangement with the outer electrode such that an approximately same distance is maintained between the inner electrode and the outer electrode at every point along the surface of the inner electrode other than proximate the support member; the space between the inner electrode an the outer electrode defining an analyzer region and, an electrical contact on at least one of the outer electrode and the inner electrode for applying a compensation voltage between the outer electrode and the inner electrode, and for applying an asymmetric waveform voltage to the at least one of the outer electrode and the inner electrode such that, during use, some ions that are introduced into an inlet region of the analyzer region are selectively transmitted through the analyzer region to an outlet region thereof along at least three different approximately shortest average ion flow paths that are other than parallel, one relative to another, along a substantial portion of a length thereof.

13. An apparatus according to claim 12, wherein the elliptical cavity is approximately spherical and wherein the ellipsoid inner electrode includes an approximately spherical outer surface.

14. An apparatus according to claim 12, comprising an inlet through a first portion of the inner curved electrode surface for introducing ions and a flow of a carrier gas into an inlet region of the internal cavity that is adjacent to the inlet, and an outlet through a second portion of the inner curved electrode surface for extracting ions from an outlet region of the internal cavity that is adjacent to the outlet.

15. An apparatus according to claim 14, wherein the first and second portions of the inner curved electrode surface are opposing surface portions.

16. An apparatus according to claim 12, wherein the outer electrode comprises a first outer electrode portion including a first inner curved electrode surface portion and a second outer electrode portion including a second inner curved electrode surface portion that is contiguous with the first inner curved electrode surface portion.

17. An apparatus according to claim 12, wherein, during use, an electric field having a similar radial profile is formed at the inlet region and at the outlet region.

* * * * *

UNITED STATES PATENT AND TRADEMARK OFFICE
CERTIFICATE OF CORRECTION

PATENT NO. : 6,713,758 B2 Page 1 of 1
DATED : March 30, 2004
INVENTOR(S) : Guevremont, Purves and Barnett

It is certified that error appears in the above-identified patent and that said Letters Patent is hereby corrected as shown below:

Title page,
Item [63], Related U.S. Application Data, should read --Continuation-in-part of application No. 09/762,239, application No. PCT/CA99/00715 on Aug. 5, 1999, which is a continuation of application No. 09/321,820, filed on May 28, 1999, now Pat. No. 6,504,149. --

Column 1,
Lines 3-11, "This application is a continuation-in-part of U.S. patent application Ser. No. 09/762,239 filed Jun. 28, 2001 which is a continuation-in-part of U.S. patent application Ser. No. 09/321,820 filed May 28, 1999 now U.S. Pat. No. 6,504,149 which is a National Stage of International Application No. PCT/CA99/00715 filed Aug. 5, 1999, which claims the benefit of U.S. Provisional Application No. 60/095,481 filed Aug. 5, 1998. This application also claims the benefit of United States Provisional Application No. 60/354,711 filed Feb. 8, 2002." should read -- This application is a continuation-in-part of U.S. patent application Ser. No. 09/762,239 filed Jun. 28, 2001 which is a National State of International Application No. PCT/CA99/00715 filed Aug. 5, 1999 and which claims the benefit of U.S. Provisional Application No. 60/095,481 filed Aug. 5, 1998. U.S. patent application Ser. No. 09/762,239, filed Jun. 28, 2001, is a continuation of application No. 09/321,820, filed May 28, 1999, now US Pat. No. 6,504,149, which also claims the benefit of U.S. Provisional Application No. 60/095,481 filed Aug. 5, 1998. The application also claims the benefit of U.S. Provisional Application No. 60/354,711 filed Feb. 8, 2002. --

Signed and Sealed this

Twelfth Day of October, 2004

JON W. DUDAS
*Director of the United States Patent and Trademark Office*